United States Patent
Weaver et al.

(10) Patent No.: US 10,596,490 B2
(45) Date of Patent: Mar. 24, 2020

(54) MULTI-PURPOSE GAS SEPARATOR UNIT AND ASSOCIATED METHODS

(71) Applicant: William Jacob Management, Inc., Houston, TX (US)

(72) Inventors: John Weaver, Houston, TX (US); Jayant Desai, Houston, TX (US); Muhammad Shahab, Houston, TX (US)

(73) Assignee: William Jacob Management, Inc., Houston, TX (US)

( * ) Notice: Subject to any disclaimer, the term of this patent is extended or adjusted under 35 U.S.C. 154(b) by 0 days.

(21) Appl. No.: 16/599,095

(22) Filed: Oct. 10, 2019

(65) Prior Publication Data

US 2020/0038780 A1    Feb. 6, 2020

Related U.S. Application Data

(62) Division of application No. 15/442,026, filed on Feb. 24, 2017, now Pat. No. 10,456,714.

(60) Provisional application No. 62/299,536, filed on Feb. 24, 2016.

(51) Int. Cl.
  *B01D 19/00* (2006.01)
  *B01D 17/02* (2006.01)
  *E21B 49/08* (2006.01)
  *G01N 33/24* (2006.01)

(52) U.S. Cl.
  CPC ..... *B01D 19/0073* (2013.01); *B01D 17/0208* (2013.01); *E21B 49/087* (2013.01); *G01N 33/24* (2013.01); *E21B 2049/085* (2013.01)

(58) Field of Classification Search
  None
  See application file for complete search history.

(56) References Cited

U.S. PATENT DOCUMENTS

| | | | | |
|---|---|---|---|---|
| 4,073,734 A | * | 2/1978 | Lowrie | B01D 17/0208 210/532.1 |
| 4,604,196 A | * | 8/1986 | Lowrie | B01D 17/0208 96/176 |
| 5,132,011 A | * | 7/1992 | Ferris | B01D 19/0042 96/184 |
| 5,415,776 A | * | 5/1995 | Homan | B01D 17/00 210/519 |

(Continued)

*Primary Examiner* — Amber R Orlando
*Assistant Examiner* — Phillip Y Shao
(74) *Attorney, Agent, or Firm* — Blank Rome LLP

(57) ABSTRACT

Inlet and outlet connections of a well manifold connect to integrated piping of a unitary vessel on a skid. The unitary vessel defines an interior separated into two chambers by a barrier. One chamber has a test inlet for well testing operation, and the other chamber has a production inlet for production operation. Each of the chambers is in communication with a gas outlet for gas, a water outlet for water, and a condensate outlet for condensate. Each of the chambers has a weir plate disposed in the chamber and separating the water outlet on a waterside of the weir plate from the condensate outlet on a condensate-side of the weir plate adjacent the barrier. During use, the second chamber can be isolated so well testing operation can be performed using the first chamber. Also, the first chamber can be isolated so production operation can be performed using the second chamber.

20 Claims, 7 Drawing Sheets

(56) References Cited

U.S. PATENT DOCUMENTS

| | | | | |
|---|---|---|---|---|
| 5,656,173 A * | 8/1997 | Jordan | ............... | B01D 17/0205 |
| | | | | 210/703 |
| 6,187,079 B1 * | 2/2001 | Bridger | ................. | B01D 17/00 |
| | | | | 96/179 |
| 6,214,220 B1 * | 4/2001 | Favret, Jr. | ............... | B01D 17/00 |
| | | | | 210/188 |
| 6,537,458 B1 * | 3/2003 | Polderman | ............. | B01D 17/00 |
| | | | | 210/801 |
| 7,347,945 B2 * | 3/2008 | Amado | ............. | B01D 17/0211 |
| | | | | 210/739 |
| 7,531,099 B1 * | 5/2009 | Rhodes | ............. | B01D 17/0211 |
| | | | | 210/800 |
| 8,088,286 B2 * | 1/2012 | Folkvang | ............... | B01D 17/00 |
| | | | | 210/188 |

* cited by examiner

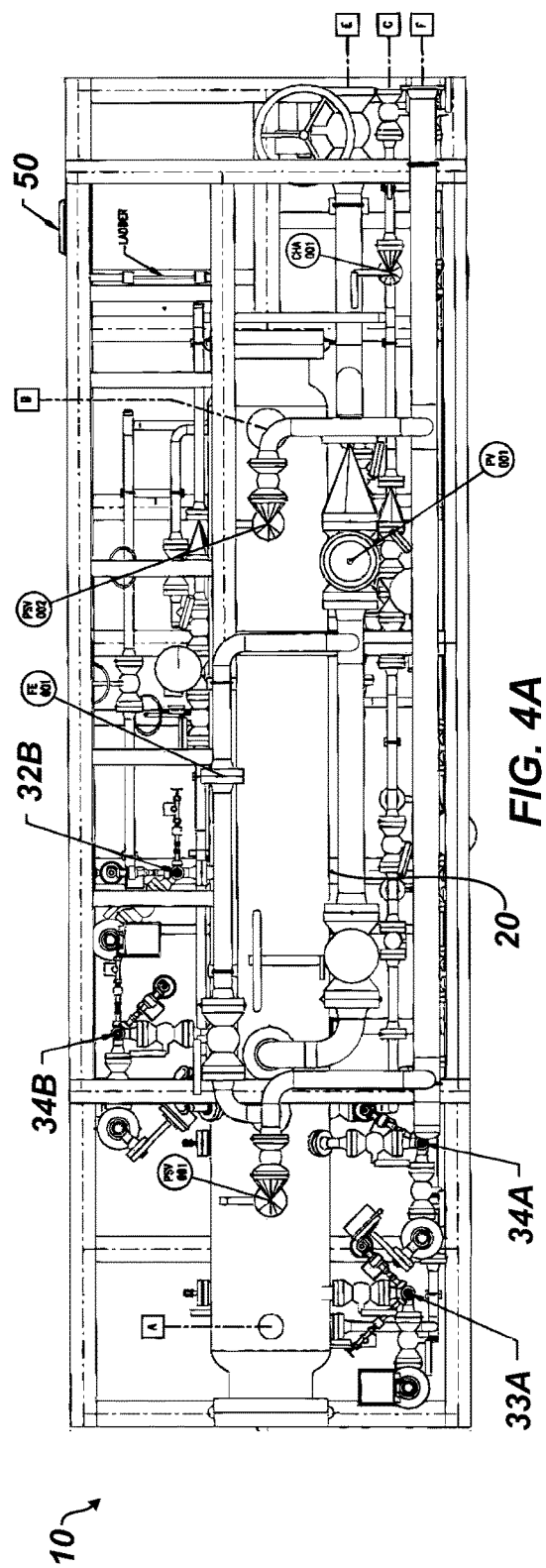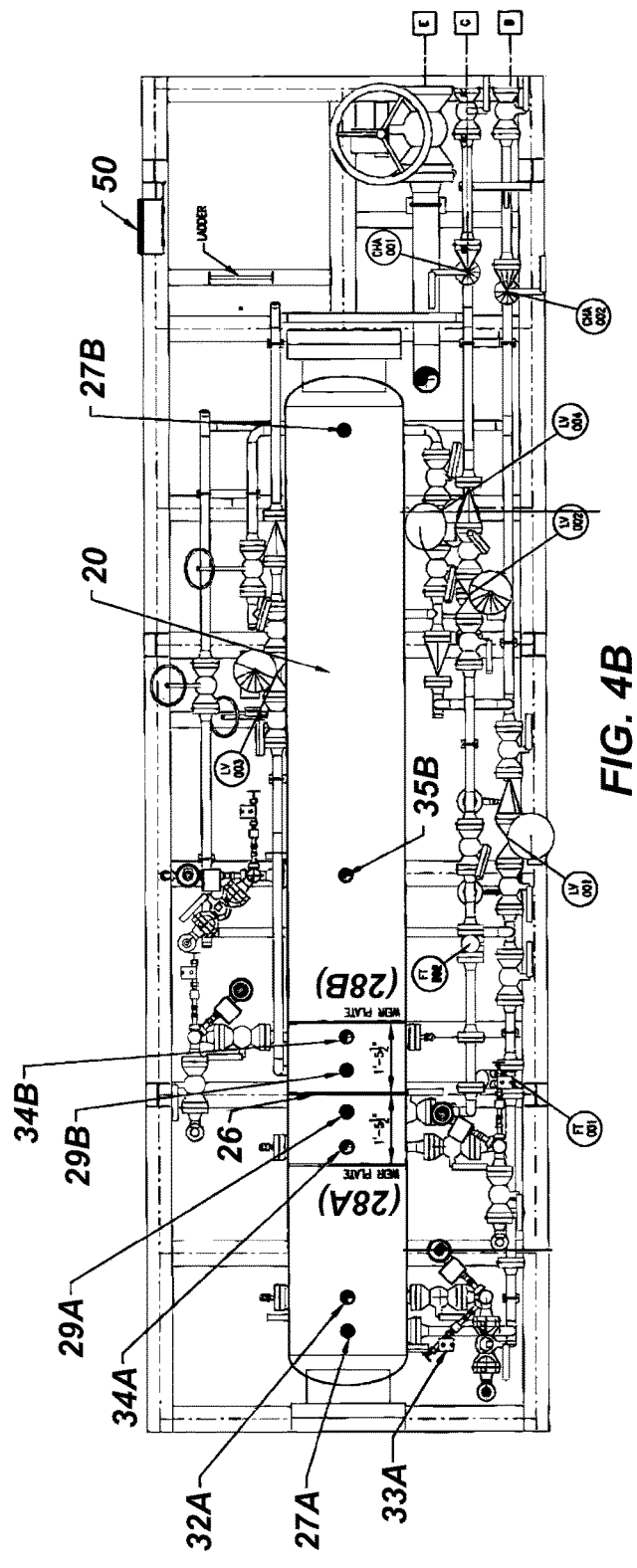
FIG. 4A
FIG. 4B

MULTI-PURPOSE GAS SEPARATOR UNIT AND ASSOCIATED METHODS

CROSS-REFERENCE TO RELATED APPLICATIONS

This application is a divisional of U.S. application Ser. No. 15/442,026, filed 24 Feb. 2017, which claims the benefit of U.S. Prov. Appl. 62/299,536, filed 24 Feb. 2016, both of which are incorporated herein by reference in its entirety.

BACKGROUND OF THE DISCLOSURE

During well operations, it is desirable at times to measure gas concentrations and the like. Typically, a gas separator is used for this purpose. Oil and water separation is necessary to make the measurements, and condensate needs to be separated so gas can be collected. To that end, wellsite installations use a production gas separator to measure gases during production of a well.

Measuring gas concentrations during well testing, however, is different from production operations. Conventionally, an individual vessel is used for production separation, while another individual vessel is used for separation to perform the well testing. When well testing and production are to be performed, the use of such individual vessels increases costs, complicates the configuration of the wellsite, and causes other recognizable problems.

The subject matter of the present disclosure is directed to overcoming, or at least reducing the effects of, one or more of the problems set forth above.

SUMMARY OF THE DISCLOSURE

A multi-purpose gas separator unit includes a unitary vessel defining an interior. The vessel has a test inlet at a first end and has a production inlet at a second, opposite end. A barrier disposed in the interior seals the interior into first and second chambers. The first chamber communicates with the test inlet and is adapted for well testing operation, while the second chamber communicates with the production inlet and is adapted for production operation. The first chamber is in communication with a first gas outlet of the vessel for gases, and the second chamber in communication with a second gas outlet of the vessel for gases.

A barrier disposed in the interior seals the interior into first and second chambers. The first chamber communicating with the test inlet is adapted for well testing operation, while the second chamber communicating with the production inlet is adapted for production operation. Each of the chambers is in communication with a gas outlet of the vessel for gas, a water outlet of the vessel for water, and a condensate outlet of the vessel for condensate. A first weir plate is disposed in the first chamber, and a second weir plate is disposed in the second chamber. Each of the weir plates separate the water outlet on a waterside of the weir plate from the condensate outlet on a condensate-side of the weir plate adjacent the barrier.

The disclosed unit can include an equalizing valve in communication between the first and second chambers of the vessel. The equalizing valve is operable to equalize the first and second chambers across the barrier. The first and second chambers can be equalized across the barrier based on a pressure differential between the inlets and outlets for the two chambers.

The barrier can include a plate welded in the interior of the vessel to seal the first and second chambers from one another.

For the first chamber adapted for testing, the disclosed unit includes a level gage for measuring an interface between water and oil on the waterside of the first weir plate and includes another level gage for measuring condensate on the condensate-side of the first weir plate. For the second chamber adapted for production, the disclosed unit includes a level gage for measuring an interface between water and oil on the waterside of the second weir plate and includes another level gage for measuring condensate on the condensate-side of the second weir plate.

A first volume of the first chamber can be less than a second volume of the second chamber. However, the volumes on the condensate sides of the first and second weir plates can be roughly the same. A relief arrangement can communicate the first and second chambers to a vent.

In use, inlet and outlet connections of a well manifold connect to integrated piping of the unitary vessel on a skid. In one setup, the second chamber can be isolated so well testing operation can be performed using the first chamber. In another set up, the first chamber can be isolated so production operation can be performed using the second chamber.

The foregoing summary is not intended to summarize each potential embodiment or every aspect of the present disclosure.

BRIEF DESCRIPTION OF THE DRAWINGS

FIGS. 4A-4B illustrate upper plan views of the disclosed unit revealing placement of various components.

DETAILED DESCRIPTION OF THE DISCLOSURE

Figure 1:
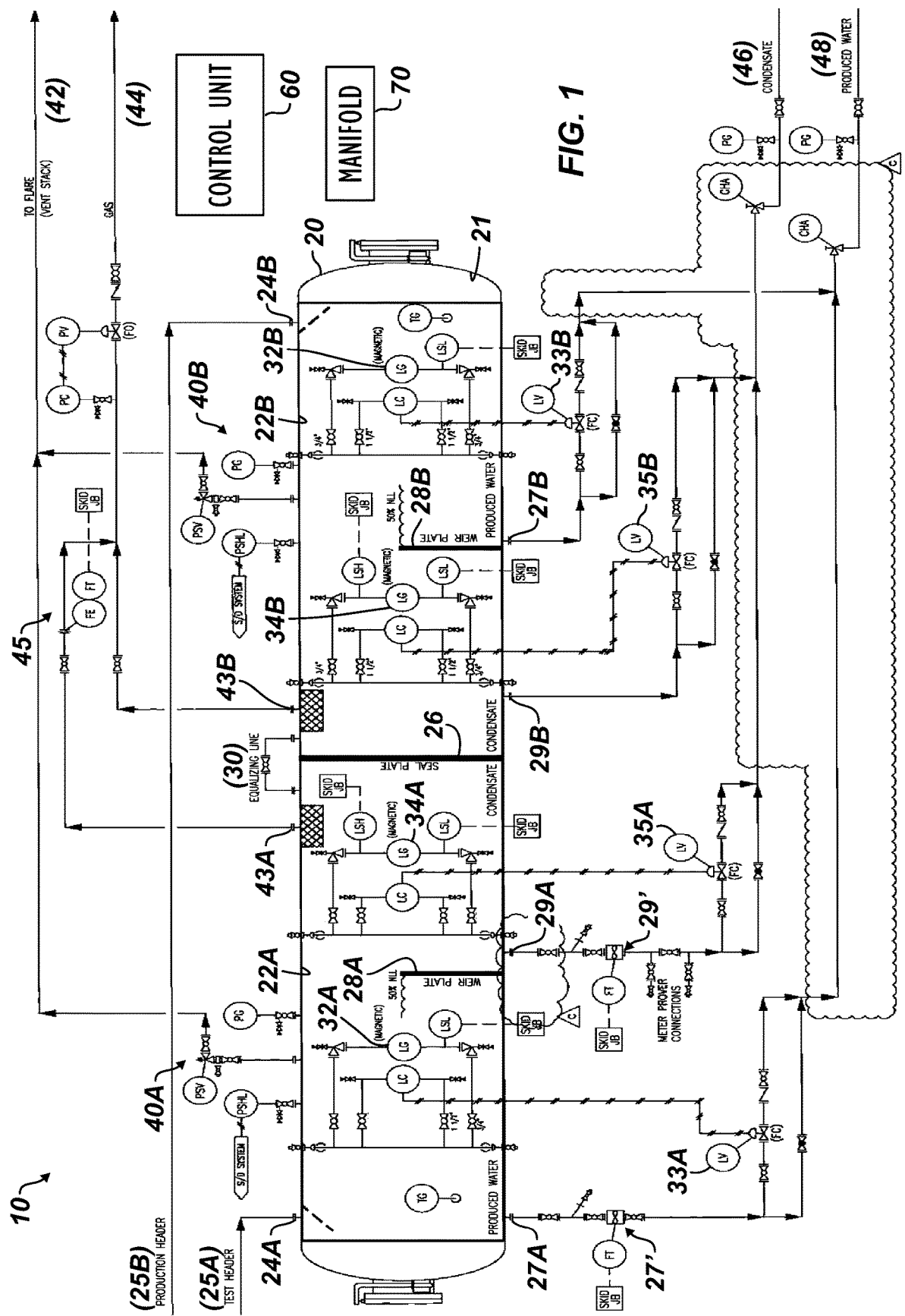
FIG. 1 illustrates a schematic of a multi-purpose gas separator unit according to the present disclosure.

FIG. 1 illustrates a schematic of a multi-purpose gas separator unit 10 according to the present disclosure. The unit 10 includes a unitary or sole pressure vessel 20 used for both well testing and production operations. The vessel 20 includes an interior 21 and can be of standard construction. Internally, the vessel 20 includes a seal plate 26 dividing the interior 21 into a test chamber 22A and a production chamber 22B. Each chamber 22A-B includes a weir plate 28A-B disposed in the vessel's interior 21 so that each chamber 22A-B acts as a 3-phase separator. Each chamber 22A-B can also include a temperature gage, a pressure gage, and other comparable components as labelled.

With more particularity, a test inlet 24A from a test header 25A enters at the top of the test chamber 22A, and a production inlet 24B from a production header 25B enters at the top of the production chamber 22B at the opposing end of the vessel 20. Between the two chambers 22A-B, the vessel 20 includes an equalizing line with a valve 30, which can be used for equalizing the two sides of the vessel 20 across the seal plate 26.

To measure the interface level between water and oil in the test chamber 22A, the unit 10 has a level gage 32A, along with appropriate level controls, valves, and piping to the chamber 22A, disposed on the water-side of the weir plate 28A. To measure the level of condensate in the test chamber 22A, the unit 10 has another level gage 34A, along with appropriate level controls, valves, and piping to the test chamber 22A, disposed on the condensate-side of the weir plate 28A.

In general and as shown, the water level gage 32A can include a magnetic level gage having a low level switch and a level controller. The level controller can be in operable communication with a level valve 33A in fluid communication with the water outlet 27A of the test chamber 22A. For its part, the condensate level gage 33A can include a magnetic level gage having a high level switch, a low level switch, and a level controller. This level controller can be in operable communication with a level valve 35A in fluid communication with the condensate outlet 29A of the test chamber 22A.

To output produced water from the test chamber 22A, a first outlet 27A connects with appropriate piping, produced water level valve 33A, and the like to a water outlet 48 of the unit 10. A flow sensor 27' and transmitter are in operable communication with the water outlet 27A of the test chamber 22A to measure the output of produced water.

To output the condensate from the test chamber 22A, a second outlet 29A connects with appropriate piping, produced condensate level valve 33A, and the like to a condensate outlet 46 of the unit 10. A flow sensor 29' and transmitter are in operable communication with the condensate outlet 29A of the test chamber 22A to measure the output of condensate.

Gases from the test chamber 22A can exit via venting 40A (shown on the waterside of the weir plate 28A) through piping, pressure safety valves, pressure gages, and the like to a vent stack or flare 42. Meanwhile, gases from the test chamber 22A can exit via a chamber outlet 43A (shown on the condensate side of the weir plate 28A) through piping, pressure valves, pressure controls, and the like to a gas outlet 44. A filter arrangement (not labeled) can communicate between outlet 43A of the chamber 22A to the piping leading to the gas outlet 44. A flow sensor 45 and transmitter are in operable communication between the chamber outlet 43A and the gas outlet 44 of the test chamber 22A.

The production side of the unit 10 is comparably arranged. As already noted, the production inlet 24B from the production header 25B enters at the top of the production chamber 22B at the waterside of the weir plate 28B. To measure the interface level between water and oil in the production chamber 22B, the unit 10 has a level gage 32B, along with appropriate level controls, valves, and piping to the chamber 22B, disposed on the waterside of the weir plate 28B. To measure the level of condensate in the production chamber 22B, the unit 10 has another level gage 34B, along with appropriate level controls, valves, and piping to the production chamber 22B, disposed on the condensate-side of the weir plate 28B.

To output produced water from the production chamber 22B, a first outlet 27B connects with appropriate piping, produced water level valve 33B, and the like to a water outlet 48 of the unit 10. To output the condensate from the production chamber 22B, a second outlet 29B connects with appropriate piping, produced condensate level valve 33B, and the like to a condensate outlet 46 of the unit 10.

Finally, gases from the production chamber 22B can exit via venting 40B (shown on the waterside of the weir plate 28B) through piping, pressure safety valves, pressure gages, and the like to a vent stack or flare 42. Meanwhile, gases from the production chamber 22B can exit via a chamber outlet 43B (shown on the condensate side of the weir plate 28B) through piping, pressure valves, pressure controls, and the like to a gas outlet 44. Again, a filter arrangement (not labeled) can communicate between the chamber outlet 43B to the piping leading to the gas outlet 44.

Figure 2A:
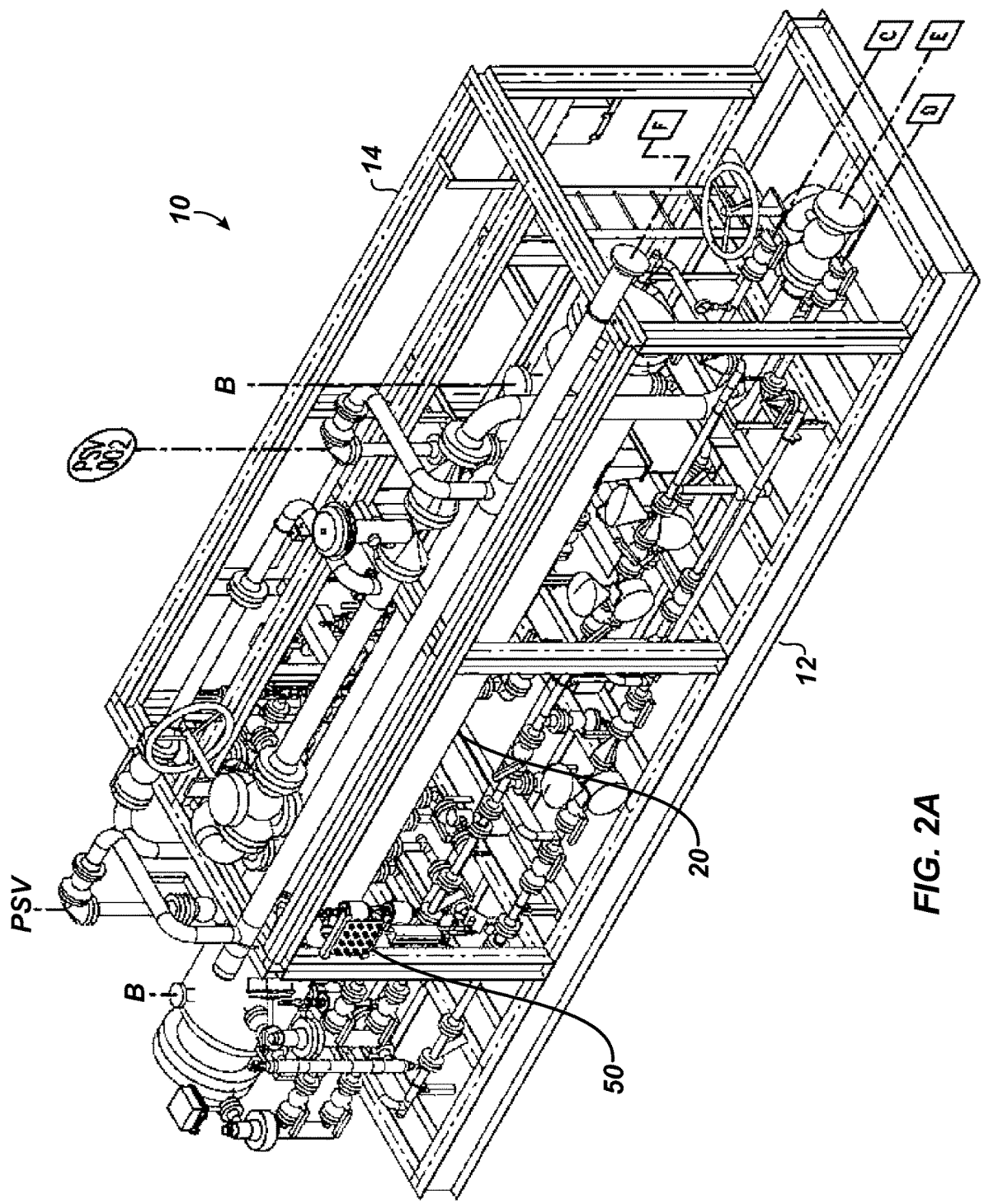
FIGS. 2A-2B illustrate isometric views of an embodiment of a first end of the disclosed unit showing the nozzle schedule and various components.
Figure 2B:
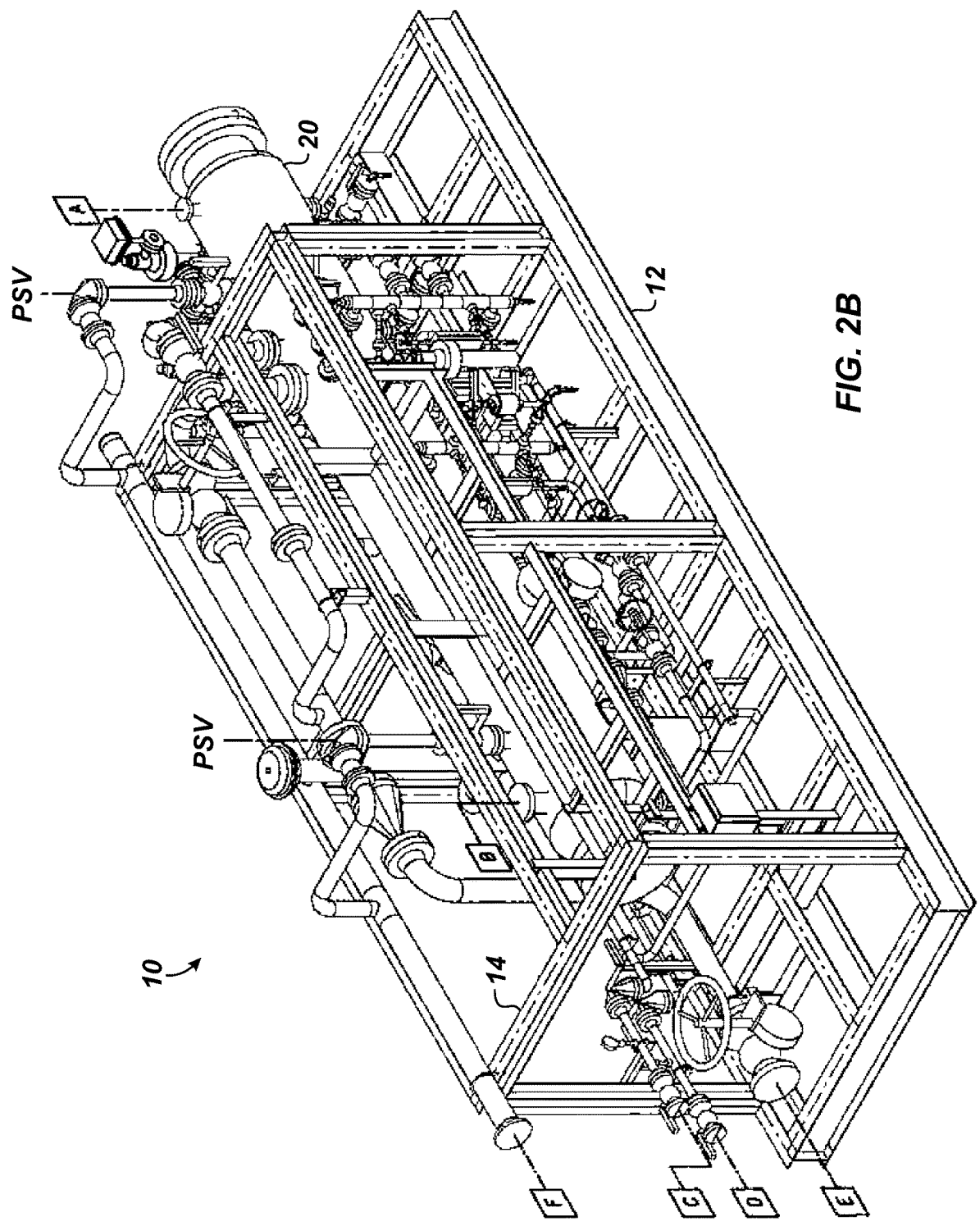
Figure 3A:
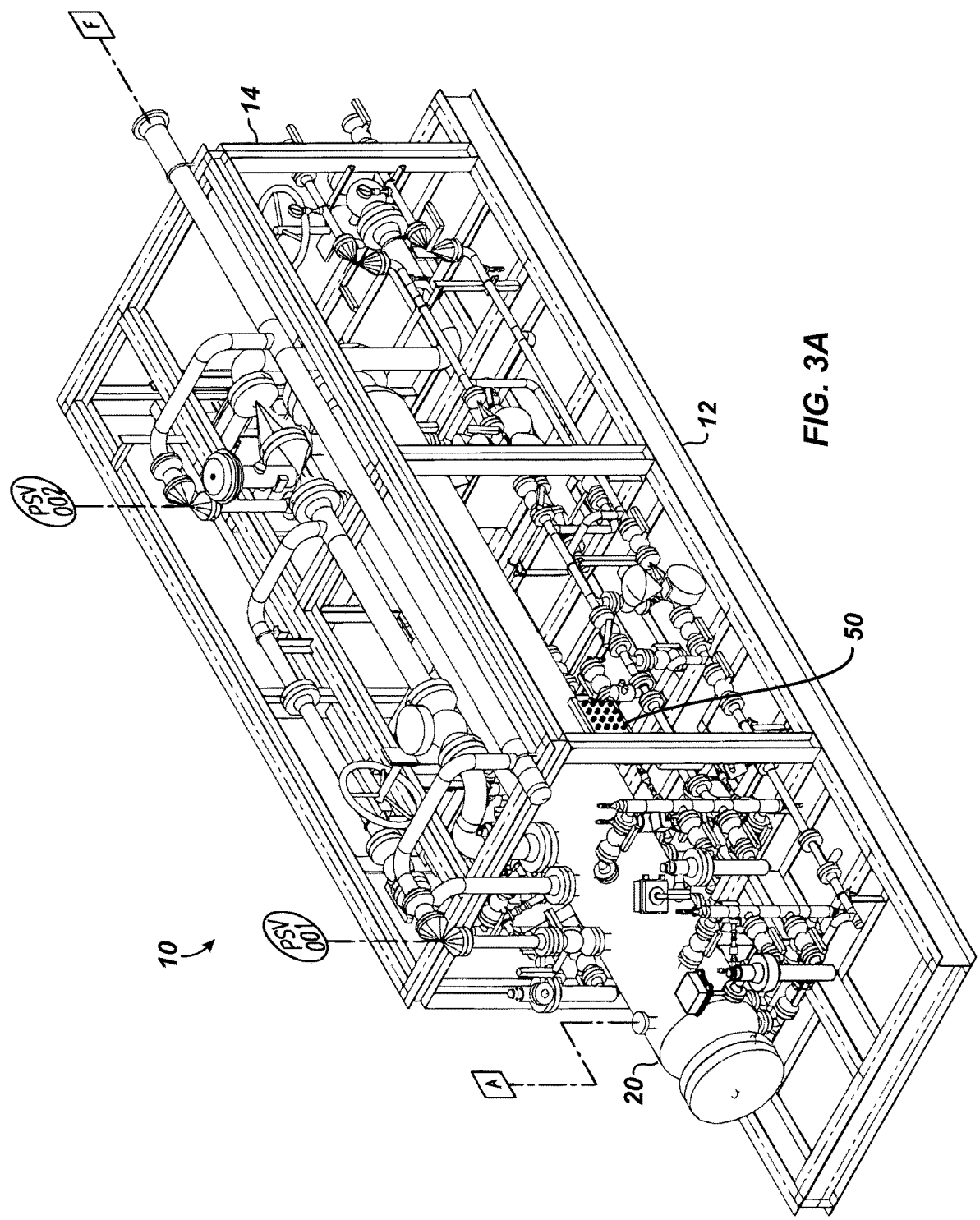
FIGS. 3A-3B illustrate isometric views of a second end of the disclosed unit showing the nozzle schedule and various components.
Figure 3B:
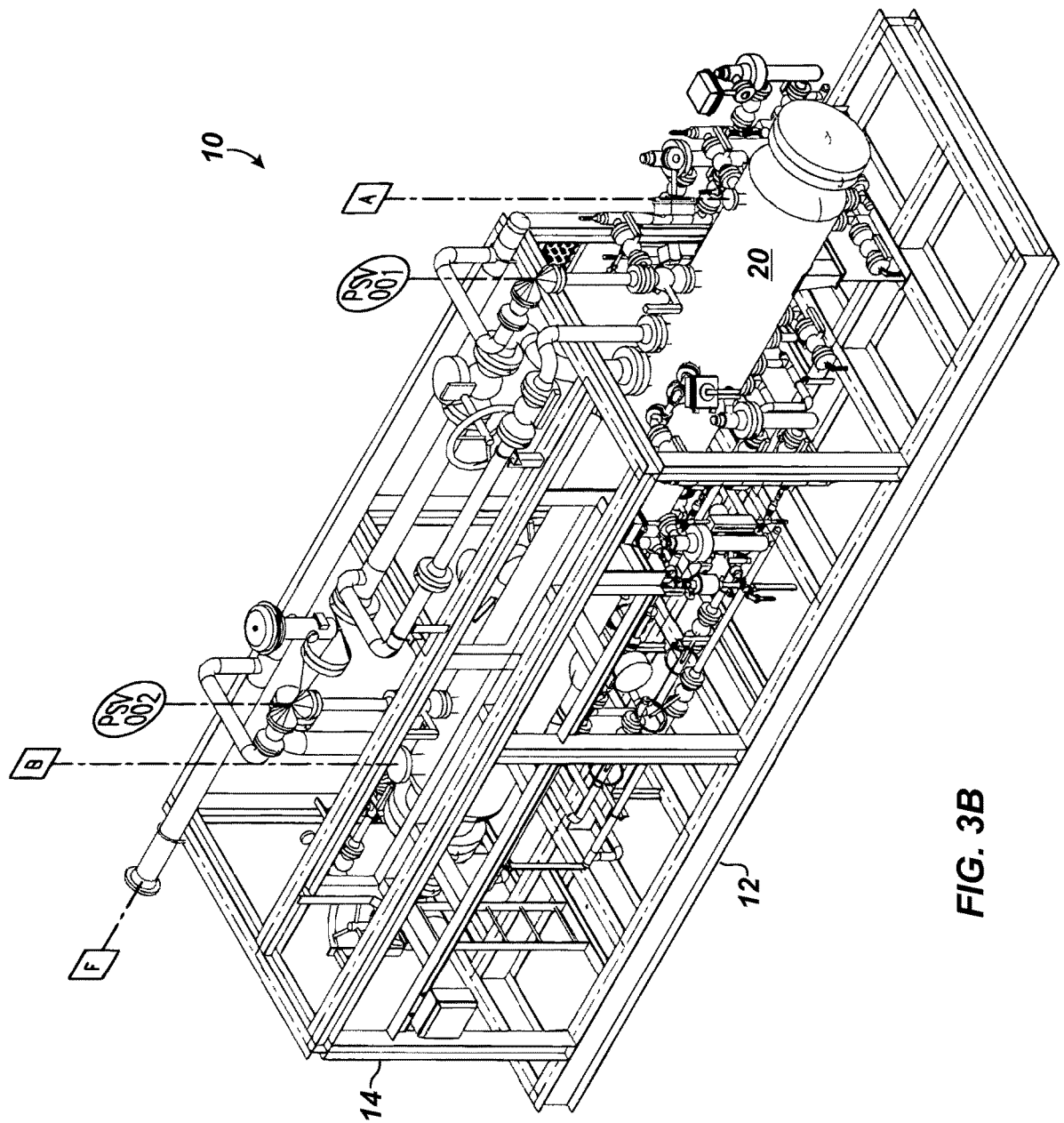

With an understanding of the schematic arrangement of the disclosed multi-purpose separator unit 10, discussion now turns to a particular configuration of the disclosed unit 20. In particular, FIGS. 2A-2B illustrate isometric views of a first end of an embodiment of the disclosed unit 10 showing the nozzle schedule and various components arranged relative to the unitary vessel 20. FIGS. 3A-3B illustrate isometric views of a second end of the disclosed unit 10.

As can be seen, the unit 10 includes a skid 12 with a surrounding frame 14 that supports the unitary vessel 20. The various piping, valves, gages, and other integrated components of the unit 10 mount about the vessel 20 in the profile of the skid 12 and the frame 14 to provide a small footprint for the unit 10. The control interface 50 for the unit 10 is accessible on the frame 14.

The nozzle connections for the unit 10 include a test inlet A, a production inlet B, a condensate outlet C, a produced water outlet D, a gas outlet E, and a relief outlet F. The test and production inlets A-B enter the top of the vessel 20 from the upper side of the skid 12 and frame 14. Advantageously, the outlets C, D, E, and F extend from one end of the skid 12 and the frame 14 to facilitate incorporating the disclosed unit 10 into the surrounding processes and piping, including a manifold 70 at the wellsite.

Figure 5A:
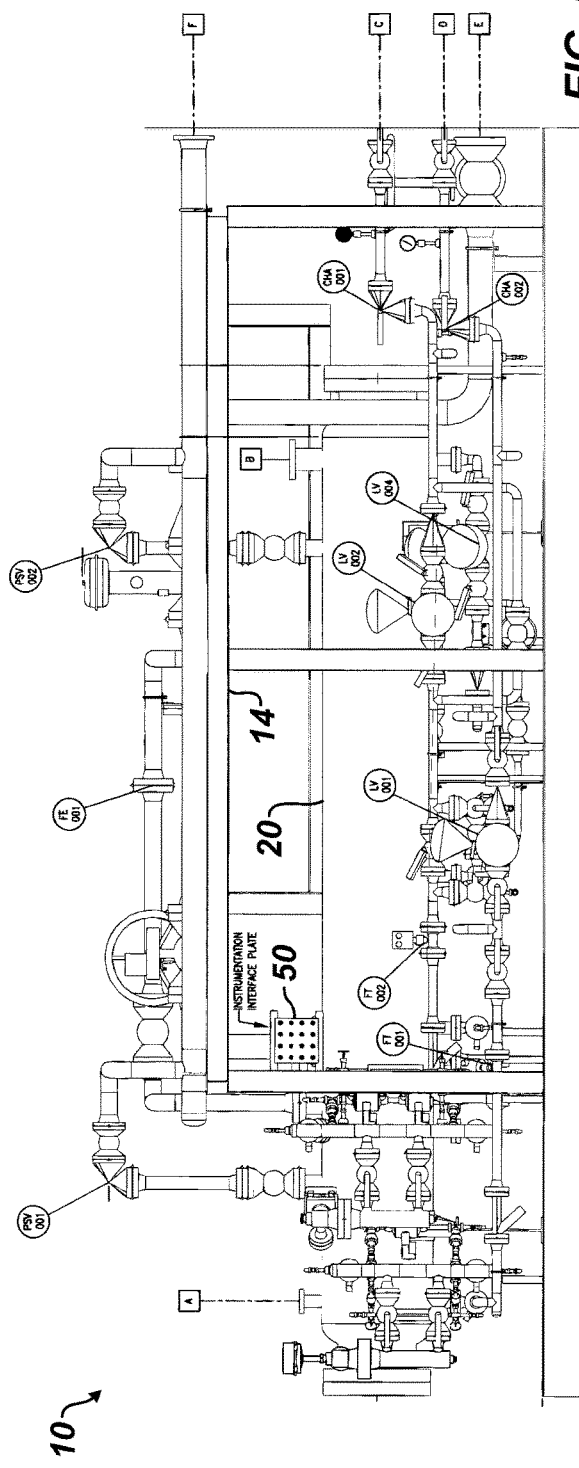
FIGS. 5A-5B illustrate elevational views of opposing sides of the disclosed unit.
Figure 5B:
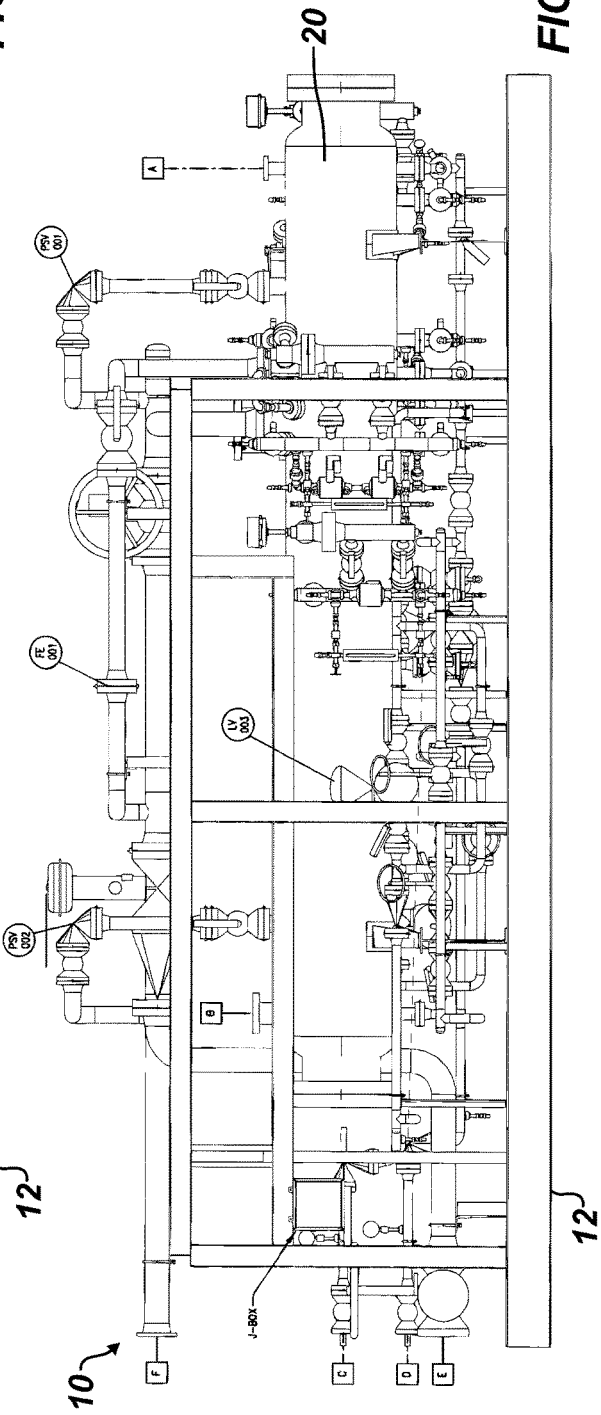

FIGS. 4A-4B illustrate the arrangement of components of the unit 10 on the skid 12 and the frame 14 in more detail. In particular, FIG. 4A shows an upper plan view of the disclosed unit 10 revealing placement of various components. FIG. 4B shows the upper plan view with elements removed to reveal the configuration of components relative to the vessel 20. Meanwhile, FIGS. 5A-5B illustrate elevational views of opposing sides of the disclosed unit 10.

As best shown in the plan view of FIG. 4B, the vessel 20 can be divided into the two chambers 22A-B to provide different volumes. As expected, the volume of the test chamber 22A can be less than that of the production chamber 22B. Therefore, the seal plate 26 in the interior 21 can be offset toward one end of the vessel 20. Placement of the inlets and outlets on the vessel 20 for the test chamber 22A are shown relative to the weir plate 28A and include a port for the water/oil interface level gage, a port for the produced water outlet, a port of the condensate water outlet, and a port for the condensate level gage. Likewise, placement of the inlets and outlets on the vessel 20 for the larger production chamber 22B is shown relative to the weir plate 28B and include a port for the production section level gage, a port for the produced water outlet, a port for the condensate water outlet, and a port for the condensate level gage. As depicted, the condensing volumes of the chambers 22A-22B on the condensate sides of the weir plates 28A-B may be comparable to one another, whereas the volume of the chambers 22A-B on the watersides of the weir plates 28A-B can be different.

The multi-purpose separator unit 10 is a separator vessel with an internal seal plate 26 dividing the vessel's interior into dual, 3-phase separators—one for testing and another for production. Accordingly, the vessel 20 with this seal plate 26 allows for simultaneous well testing and production. This dual capability makes the disclosed separator unit 10 unique to all other separator configurations that consist of an individual vessel for production separation and another individual vessel for separation to perform well testing. The seal plate 26 is positioned for a single well test while the remaining portion of the vessel 20 is dedicated to conventional separation to accommodate the basis of design.

The multi-purpose separator unit 10 can be pressure balanced by the production manifold 70 or by the vessel equalizing valve 30 installed upstream and downstream of the seal plate 26. In essence then, the disclosed separator unit 10 offers one vessel serving two purposes, which is achievable with the pressure-balanced internal seal plate 26 between the test and production chambers 22A-B.

Operations initially entail isolating the production section (e.g., chamber 22B, etc.) from the test section (e.g., chamber 22A, etc.). Well testing can begin at that point. Then, operations involve switching via the manifold 70 to the production section while opening the necessary isolation valves.

Instrumentation and controls for the multi-purpose separator unit 10 can be comparable to those used for a typical independent test separator and a typical independent production separator. Of course, the dual controls for the disclosed separator unit 10 can be integrated together in the separator's unitary control unit 60 to achieve both testing and production operations.

Because the multi-purpose separator unit 10 includes the dual functionality, the disclosed unit 10 can take up less deck space offshore. Naturally, the overall weight of the disclosed separator unit 10 can be more manageable, and any civil or structural foundations for supporting the unit can be less costly.

The foregoing description of preferred and other embodiments is not intended to limit or restrict the scope or applicability of the inventive concepts conceived of by the Applicants. It will be appreciated with the benefit of the present disclosure that features described above in accordance with any embodiment or aspect of the disclosed subject matter can be utilized, either alone or in combination, with any other described feature, in any other embodiment or aspect of the disclosed subject matter.

As will be appreciated, various details related to dimensions, pressure ratings, types of valves, etc. have been omitted as being understood by the standard practices of one skilled in the art. Suffice it to say that the disclosed unit 10 can be properly configured to meet the requirements of a given implementation in accordance with such standard practices without departing from the teachings of the present disclosure.

In exchange for disclosing the inventive concepts contained herein, the Applicants desire all patent rights afforded by the appended claims. Therefore, it is intended that the appended claims include all modifications and alterations to the full extent that they come within the scope of the following claims or the equivalents thereof.

What is claimed is:

1. A method for use with a manifold having inlet and outlet connections, the method comprising:
   connecting the inlet connections of the manifold to integrated piping of a unitary vessel, the unitary vessel having an interior sealed into first and second chambers by a barrier disposed in the interior, the first chamber in communication with a first inlet, the second chamber in communication with a second inlet;
   connecting the outlet connections of the manifold to the integrated piping of the unitary vessel, each of the first and second chambers in communication with a respective gas outlet for gas, a respective water outlet for water, and a respective condensate outlet for condensate, each of the first and second chambers having a respective weir plate disposed therein and separating the respective water outlet on a waterside of the respective weir plate from the respective condensate outlet on a condensate-side of the respective weir plate; and
   isolating the second chamber and performing a first operation using the first chamber.

2. The method of claim 1, wherein performing the first operation using the first chamber comprises:
   measuring the water of the first chamber and controlling output of the water from the respective water outlet of the first chamber;
   measuring the condensate of the first chamber and controlling output of the condensate from the respective condensate outlet of the first chamber; and
   measuring the gas of the first chamber and controlling output of the gas from the respective gas outlet of the first chamber.

3. The method of claim 1, further comprising isolating the first chamber and performing a second operation using the second chamber.

4. The method of claim 3, wherein performing the first operation using the first chamber comprises performing a well testing operation using the first chamber; and wherein performing the second operation using the second chamber comprises performing a production operation using the second chamber.

5. The method of claim 4, further comprising integrating dual controls of the unitary vessel for both of the well testing and production operations with a unitary control unit.

6. The method of claim 4, wherein performing the well testing operation using the first chamber comprises using the first chamber defining a first volume; and wherein performing the production operation comprises using the second chamber defining a second volume, the first volume being less than the second volume.

7. The method of claim 6, wherein performing the well testing operation using the first chamber comprises using a first volume portion of the first volume on the condensate-side of the respective weir plate; and wherein performing the production operation comprises using a second volume portion of the second volume on the condensate-side of the respective weir plate, the second volume portion equivalent to the first volume portion.

8. The method of claim 1, wherein performing the first operation using the first chamber comprises:
   measuring, with a first level gage, a first interface between the water and oil on the waterside of the respective weir plate; and
   measuring, with a second level gage, the condensate on the condensate-side of the respective weir plate.

9. The method of claim 8,
   wherein measuring with the first level gage comprises measuring with a first magnetic level gage having a first low level switch and a first level controller; and wherein performing the first operation comprises controlling a first level of the water with the first level controller in operable communication with a first level valve in fluid communication with the respective water outlet of the first chamber; and
   wherein measuring with the second level gage comprises a second magnetic level gage having a high level switch, a second low level switch, and a second level controller; and wherein performing the first operation comprises controlling a second level of the condensate with the second level controller in operable communication with a second level valve in fluid communication with the respective condensate outlet of the first chamber.

10. The apparatus of claim 8, further comprising isolating the first chamber and performing a second operation using the second chamber, wherein performing the second operation using the second chamber comprises:
measuring, with a third level gage, a second interface between the water and the oil on the waterside of the respective weir plate of the second chamber; and
measuring, with a fourth level gage, the condensate on the condensate-side of the respective weir plate of the second chamber.

11. The method of claim 10,
wherein measuring with the third level gage comprises measuring with a first magnetic level gage having a first low level switch and a first level controller; and wherein performing the second operation comprises controlling a first level of the water with the first level controller in operable communication with a first level valve in fluid communication with the respective water outlet of the second chamber; and
wherein measuring with the fourth level gage comprises a second magnetic level gage having a high level switch, a second low level switch, and a second level controller; and wherein performing the second operation comprises controlling a second level of the condensate with the second level controller in operable communication with a second level valve in fluid communication with the respective condensate outlet of the second chamber.

12. The method of claim 1, wherein performing the first operation comprises measuring flow with a first flow sensor in operable communication with the respective condensate outlet of the first chamber, a second flow sensor in operable communication with the respective gas outlet of the first chamber; and a third flow sensor in operable communication with the respective water outlet of the first chamber.

13. The method of claim 1, further comprising measuring a temperature and a pressure in each of the first and second chambers with a respective temperature gage and a respective pressure gage in communication with each of the first and second chambers.

14. The method of claim 1, further comprising equalizing the first and second chambers across the barrier with an equalizing valve in communication between the first and second chambers of the unitary vessel.

15. The method of claim 14, wherein equalizing the first and second chambers across the barrier comprises equalizing the first and second chambers across the barrier based on a pressure differential between the respective inlets and outlets for the first and second chambers.

16. The method of claim 1, further comprising supporting the unitary vessel and integrated piping on a skid.

17. The method of claim 16, wherein connecting the outlet connections of the manifold to the integrated piping of the unitary vessel comprises connecting to a first connection end disposed at one end of the skid for the respective condensate outlets of the first and second chambers combined, a second connection end disposed at the one end of the skid for the respective water outlets combined, and a third connection end disposed at the one end of the skid for the respective gas outlets combined.

18. The method of claim 16, wherein connecting the inlet connections of the manifold to the integrated piping of the unitary vessel comprises connecting to a first connection end disposed at a side of the skid for the first inlet, and a second connection end disposed at the side of the skid for the second inlet.

19. The method of claim 1, comprising welding a plate in the interior of the unitary vessel, and sealing the first and second chambers from one another with the welded plate as the barrier.

20. A method for use with a manifold having inlet and outlet connections, the method comprising:
connecting the inlet connections of the manifold to integrated piping of a unitary vessel, the unitary vessel defining an interior, a barrier disposed in the interior of the unitary vessel sealing the interior into first and second chambers, the first chamber having a test inlet, the second chamber having a production inlet;
connecting the outlet connections of the manifold to the integrated piping of the unitary vessel, each of the first and second chambers in communication with a respective gas outlet for gas, a respective water outlet for water, and a respective condensate outlet for condensate, each of the first and second chambers having a respective weir plate disposed in the respective chamber and separating the respective water outlet on a waterside of the respective weir plate from the respective condensate outlet on a condensate-side of the respective weir plate;
isolating the second chamber and performing a well testing operation using the first chamber; and
isolating the first chamber and performing a production operation using the second chamber.

* * * * *